United States Patent [19]
Paz-Pujalt et al.

[11] Patent Number: 5,399,315
[45] Date of Patent: Mar. 21, 1995

[54] TEST ELEMENT FOR OPTICALLY TESTING BIOLOGICAL FLUIDS IN CLINICAL DIAGNOSTIC APPLICATIONS

[75] Inventors: Gustavo R. Paz-Pujalt; Charles R. Moon, both of Rochester, N.Y.

[73] Assignee: Eastman Kodak Company, Rochester, N.Y.

[21] Appl. No.: 242,487

[22] Filed: May 13, 1994

[51] Int. Cl.$^6$ ............................................. G01N 31/22
[52] U.S. Cl. ........................................ 422/56; 422/57; 422/58; 422/82.05; 436/170
[58] Field of Search ..................... 422/56–58, 422/82.05, 82.08; 436/169, 170, 172

[56] References Cited

U.S. PATENT DOCUMENTS 3,992,158  11/1976  Przybylowicz et al. ............. 422/56
5,102,786   4/1992  Cohen et al. ........................ 422/56

*Primary Examiner*—Jill A. Warden
*Attorney, Agent, or Firm*—Raymond L. Owens

[57] ABSTRACT

An integral test element for analysis of liquids comprising: a) a spreading layer for uniformly spreading within itself at least a substance of a liquid sample applied to the element; b) a reagent layer in fluid contact with the spreading layer and permeable to a substance spreadable within the spreading layer or to a reaction product of such a substance, the reagent layer having a chemically interactive material which, in the presence of the substance or of the reaction product of the substance, produces a detectable change in the element; and c) a radiation upconversion phosphor layer or crystal for producing an upconverted radiation when excited by visible or infrared excitation radiation from an independent source.

7 Claims, 4 Drawing Sheets

TEST ELEMENT FOR OPTICALLY TESTING BIOLOGICAL FLUIDS IN CLINICAL DIAGNOSTIC APPLICATIONS

CROSS REFERENCE TO RELATED APPLICATIONS

Reference is made to commonly assigned U.S. Ser. No. 186,400, filed Jan. 25, 1994, entitled "Device Converting Invisible and Visible Radiation to Visible Light and/or UV Radiation", of Gustavo R. PazPujalt et al, and U.S. Ser. No. , 242,482, filed concurrently herewith, entitled "A Method of Using Multiwavelength Upconversion For Sample Element Interrogation In Medical Diagnostic Equipment" by PazPujalt et al, the disclosures of which are incorporated herein by reference.

FIELD OF THE INVENTION

The present invention relates to integrated test elements for optically testing biological fluids for clinical diagnostic applications.

BACKGROUND OF THE INVENTION

Chemical analysis of a test element often involves the use of UV/visible radiation from 300 nm to 700 nm, to determine quantitatively the composition of liquids like water, foodstuffs or biological fluids like serum. Reflectance or transmission density, or fluorescence measurements of the test element can be used to calculate chemical concentrations thereby providing a more complete picture of a patients condition.

In dry chemistry blood analysis (as used herein, "dry chemistry" refers to tests wherein there are no liquid reagents stored for use, such tests being possible by test elements of the type described in U.S. Pat. No. 3,992,158, issued Nov. 16, 1976), a sample of blood serum, is added to a test element containing chemical reagents. After sufficient incubation time, a color change or fluorescence is detected by a radiometer. The following is a typical example of a colorimetric test for albumin:

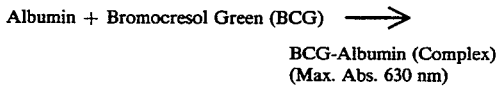

where the BCG-Albumin complex, formed upon the interaction of albumin with the indicator bromocresol green (BCG), absorbs radiation and the absorption maximum is at 630 nm. The degree of radiation absorption can be monitored as a measure of the albumin concentration.

These tests can be performed, as described in U.S. Pat. No. 3,992,158, issued Nov. 16, 1976, in clinical chemistry slides. The test element shown in FIG. 1 includes a multilayered analytical element coated on a clear polymeric support 12 held in a slide mount 11. The top layer 18 is an isotropically porous spreading layer which evenly distributes the fluid to be analyzed into the underlaying reagent layers 20, that may perform multiple functions in an integrated manner.

The trend in this industry is toward smaller more compact instruments such that their use could be extended to smaller institutions and individual practices.

The prior art includes several types of light sources that can be used for making measurements in the 300 nm to 700 nm range such as tungsten halogen and pulsed xenon lamps. One of the problem associated with these radiation sources is their relatively low stability, short life, size, and lack of compactness and ruggedness. Although there is a high ratio of usable radiant energy with respect to power and heat generated, the measurement of that power is limited to a short time. High voltages and sudden surges of high current generate electrical noise that often interferes with other electronic subsystems. Furthermore tungsten halogen lamps have relatively short lives, generate excessive heat, and have a low ratio of usable light to power in the UV-blue region of the spectrum. In addition the output power or intensity decreases with time and with filament life.

These lamps, in general, are large and cumbersome and require frequent adjustments and replacement because of burned out filaments. In addition these lamps preclude efforts to miniaturize such equipment and also pose a potential danger to operators and to the equipment itself because of the heat generated during their operation. The wavelengths produced may vary as a function of time with the aging of the lamps, and because the process involves Ar or halogen gases that have to be "ignited" in order to produce radiation, it is not possible to modulate these lamps at rates faster than what a mechanical shutter would provide.

FIG. 2 shows a schematic of a prior art system. As shown in FIG. 2, light produced by a lamp 47 is passed through an upconversion device 48, an infrared filter 50 and is reflected off of a second (cold) mirror 52 which absorbs infrared radiation through an aperture arrangement 54 on through a series of lenses 56 where a light is focused onto a sample deposited on a slide 58. The sample includes a liquid that has an active biological fluid and a chemically interactive material. See the discussion in the Background of the Invention. Light which is reflected off of the slide through the biological fluid passes through a collimated lens assembly 60 and then a relay lens assembly 62 where it is focused onto a photodetector 59. Intermediate between the collimated lens assembly 60 and the relay lens assembly 62 there is provided a filter wheel 64 through which appropriate filters can be placed into the optical path of the light between the collimated lens assembly 60 and the relay lens assembly 62. The filters are used to select the spectrum of light that will interact with the chemically active material found in the test element. The sample containing the biological fluid also contains a chemically active material, that can be activated in the presence of such material to produce a quantitative and detectable change which can be the generation or destruction of coloration or fluorescence. Besides the above discussed lighting problems, one of the drawbacks of such an approach lies in the fact that it requires a large number of optical elements to guide the "interrogating radiation" into the slide. Furthermore, it requires to bring the UV radiation from an external source along with the special handling requirements of such UV radiation.

SUMMARY OF THE INVENTION

Accordingly, it is an object of the present invention to provide an improved test element for optically testing biological fluids for clinical diagnostic applications that overcomes the drawbacks mentioned in the above discussion with respect to conventional testing elements or methods.

This object is achieved by providing an integral test element for analysis of liquids comprising:
  a) a spreading layer for uniformly spreading within itself at least a substance of a liquid sample applied to the element;
  b) a reagent layer in fluid contact with the spreading layer and permeable to a substance spreadable within the spreading layer or to a reaction product of such a substance, said reagent layer having a chemically interactive material which, in the presence of the substance or of the reaction product of the substance, produces a detectable change in the element; and
  c) a radiation upconversion phosphor layer for producing upconverted radiation when excited by visible or infrared excitation radiation from an independent source.

These and other objects of the present invention will become more apparent when taken in conjunction with the following description and drawings wherein like characters indicate like parts and which drawings form a part of the present description.

The following are advantages of the present invention: the presence of a radiation source in-situ eliminates the need of complicated lighting and optics systems as those used by the prior art i.e. halogen, tungsten filament, or xenon lamps thereby making it possible to reduce the size of the equipment. Intimate contact of the radiation source and the analyte may increase the detection limits. The radiation source described herein operates at relatively low temperatures (room temperature). The upconversion process does not generate heat. The all solid state radiation source consumes low electrical powers when compared with a lamp. The use of an upconversion phosphor material integrated onto the test element can potentially reduce the number of optical elements necessary to guide the interrogating radiation into the slide and the dye layer may be targeted more optimally for interrogation. Integration permits the possibility of optimizing the use of antireflection and reflection coatings to ensure the best possible interaction of the interrogating radiation with the dye layer. Furthermore integration of the UV radiation source eliminates the need to bring the UV radiation from an external source and thus alleviates special handling requirements of UV radiation. Changes in the nature of the constituents of the upconversion phosphor material result in different upconversion wavelengths without having to switch to new sources. Several different upconversion phosphor materials can share the same upconversion source leading to multiple combinations of wavelengths for purposes of sample interrogation. Depending on the absorption bandwidth of the interrogated species multiwavelength measurements may be conducted thus facilitating multivariate regression.

DESCRIPTION OF THE PREFERRED EMBODIMENTS

Figure 1:
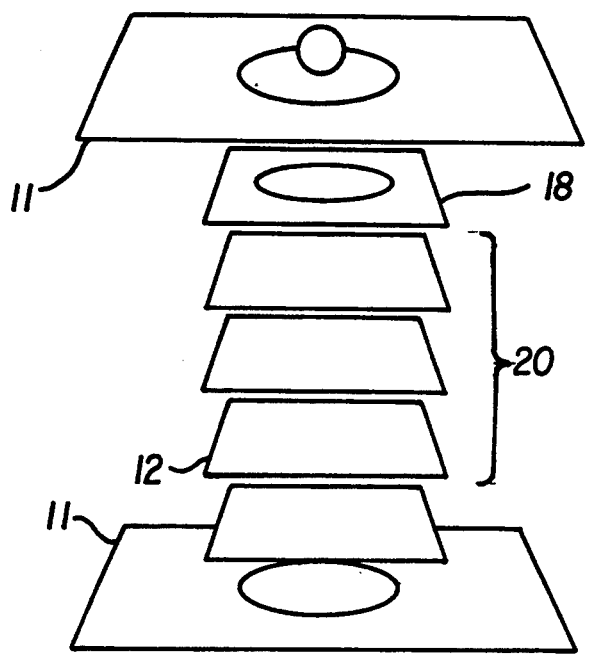
FIG. 1 illustrates the multilayered structure of a conventional test element.
Figure 3:
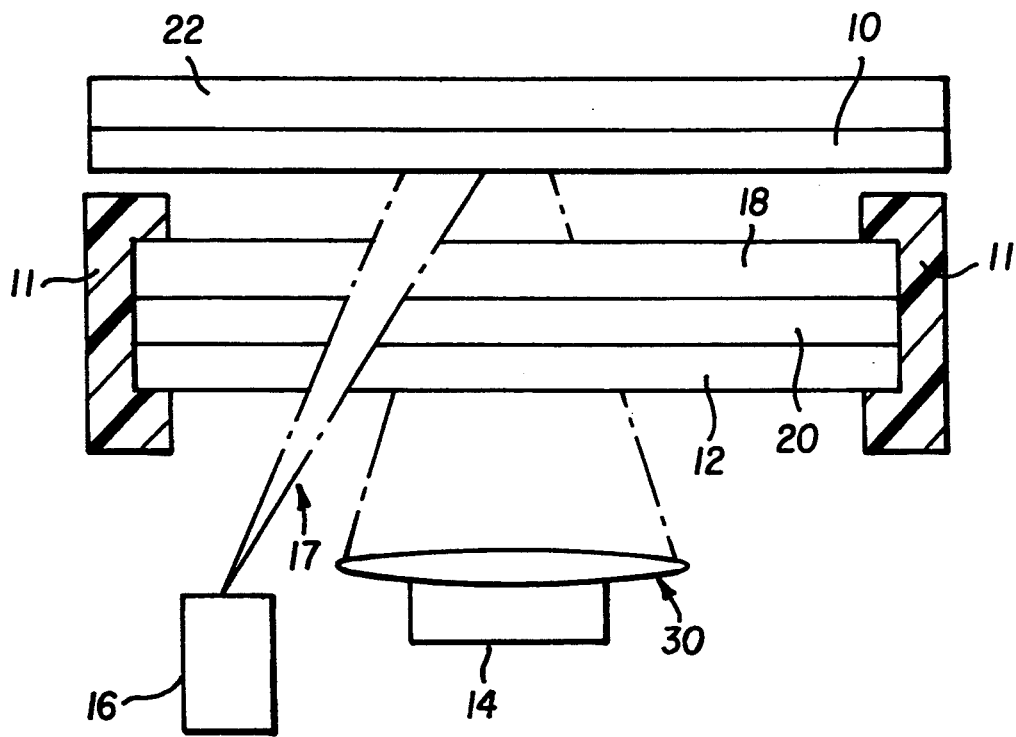
FIG. 3 illustrates a first embodiment of the test element according to the invention.
Figure 2:
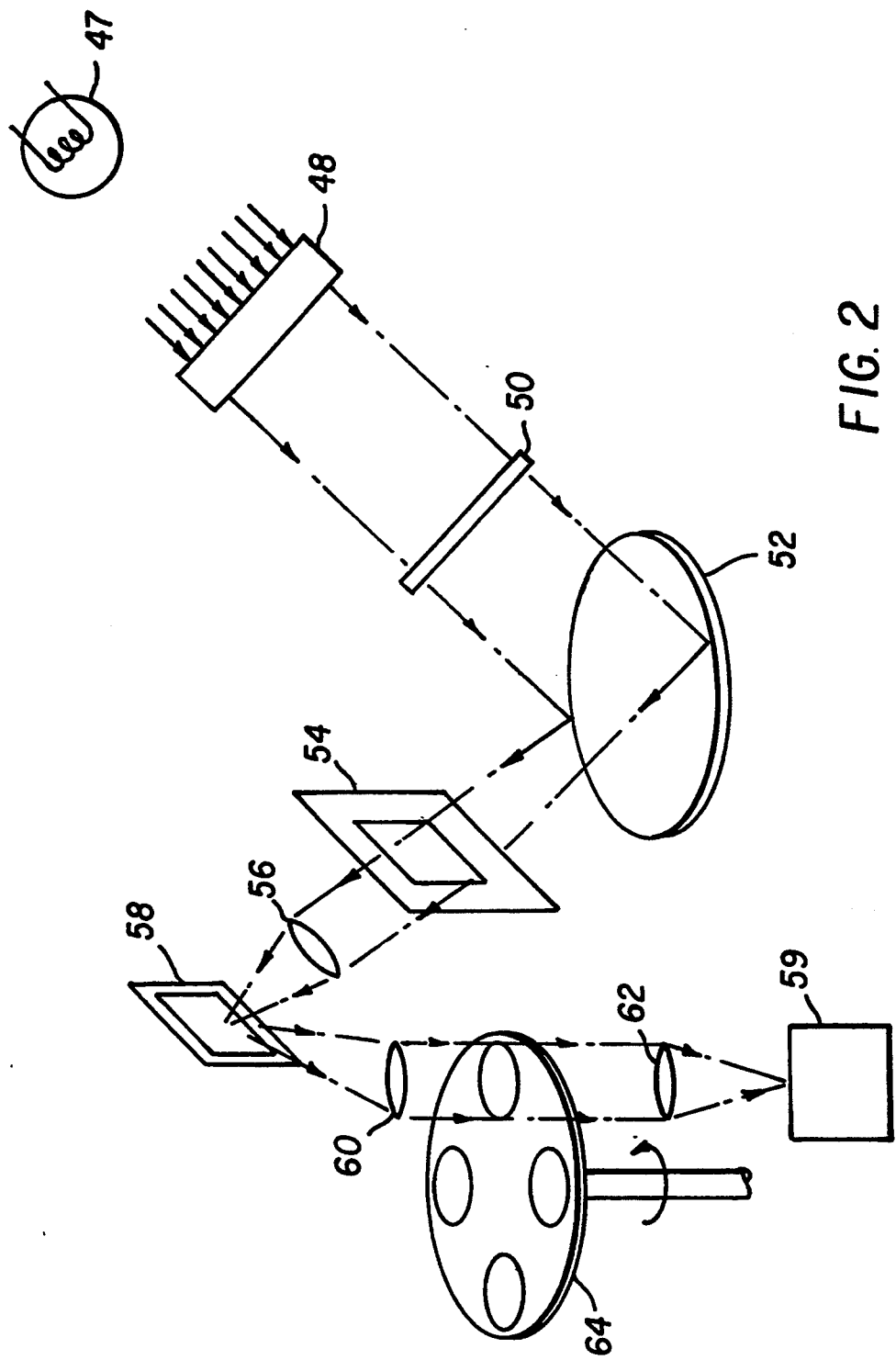
FIG. 2 shows a schematic of a prior system.

FIG. 3 illustrates a first embodiment of a test element according to the invention. Where parts correspond to those in FIG. 1, the same numerals will be used. The test element consists of an integral frame having an analytical part including one or more reagent layers 20. Preferably, this arrangement of different layers is held in a test element or slide mount 11. The reagent layers can be coated on a support 12 such as a clear polymeric support. A spreading layer 18, which can be an isotropically porous layer, spreads within itself at least a component of a liquid sample applied to the test element, or a reaction product of such a component to obtain a uniform concentration of at least one such spread substance at the surface of the spreading layer 18 which faces the reagent layers 20. The reagent layer 20, which is desirably uniformly permeable to at least one dissolved or dispersed component of the liquid sample or a reaction product of such a component, can include a matrix in which is distributed a material that can interact with, for example, an analyte or an analyte reaction product to produce a detectable change in the element, such as one detectable by measurement of electromagnetic radiation. In a preferred embodiment, the interactive material can chemically react with an analyte or analyte reaction product to produce a color change in the element.

In another preferred embodiment, the sample spreading layer 18 can filter out chemically interfering or other undesirable materials and obtain selective spreading of sample components and/or it can provide a reflective background, often useful in obtaining analytical results.

Also integrated in the test element is an upconversion phosphor in layer or crystal 10 exhibiting upconversion radiation when excited by visible or infrared irradiation from an independent source 16. According to a particular embodiment, the upconversion phosphor in layer or crystal is selected from a crystalline or amorphous layer containing a rare-earth metal fluoride capable of interacting with red or infrared radiation and converting such to ultraviolet or visible radiation. As an example, the upconversion phosphor can be selected from a mixed metal fluoride including alkaline fluorides, alkaline earth fluorides, and lanthanide fluorides. More precisely, the upconversion film can be an amorphous phosphor thin film in a family of glass upconversion phosphors of the following composition:

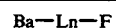

where Ln may be Y, Yb, Ho, Er, Tm or a combination thereof. One of the advantages of these family of phosphors over heavy metal fluoride phosphors is that the vapor pressures for the constituent fluorides can be closely matched, making them ideal for thermal deposition and electron-beam (e-beam) deposition to form thin films.

The test element is, of course, irradiated by light, preferably from a laser and such light can be modulated by a modulator to produce pulses of irradiation. Other details on this upconversion phosphor layer 10 can be found in the above mentioned related applications.

According to the embodiment shown in FIG. 3, the upconversion phosphor material 10 is supported by an evaporation prevention cap 22 for the dry slide. Where elements correspond to those in FIG. 1, discussed above, the same numerals will be used. The cap and supported upconversion layer are such that when positioned on the test element, the arrangement defines a one-piece element. A source of irradiation 16 produces a beam that passes though the support 12, the reagent layer 20, and the spreading layer 18 to interact with the upconversion phosphor material contained in the evaporation cap 22; and is detected by an appropriate detector 14 after interacting with the reagent layer 20.

In operation, a biological fluid is deposited on the test element. The biological fluid interacts with the spreading layer 18 to disperse the biological fluid laterally. The biological fluid penetrates into the subsequent reagent layer(s) 20 where a characteristic chemical reaction takes place with reactant(s) contained in the layer giving a characteristic color change. In-situ phosphor layer(s) 10 interacts with an independent radiation source like a light emitting diode (LED) or a diode laser or other suitable source producing upconversion radiation in the red-green-blue and ultra-violet (RGB-UV) regions. The upconversion radiation interacts with the sample or analyte absorbing a characteristic radiation wavelength ($\lambda$) in a manner proportional to the concentration of the analyte. Comparison of the degree of radiation absorption against a standard of known composition or in a look-up table produces a quantitative measure of such analyte.

In this invention, an upconversion phosphor material capable of converting visible or infrared radiation into RGB-UV which is particularly suitable for interrogating test samples having a biological fluid deposited thereon is used.

Figure 4:
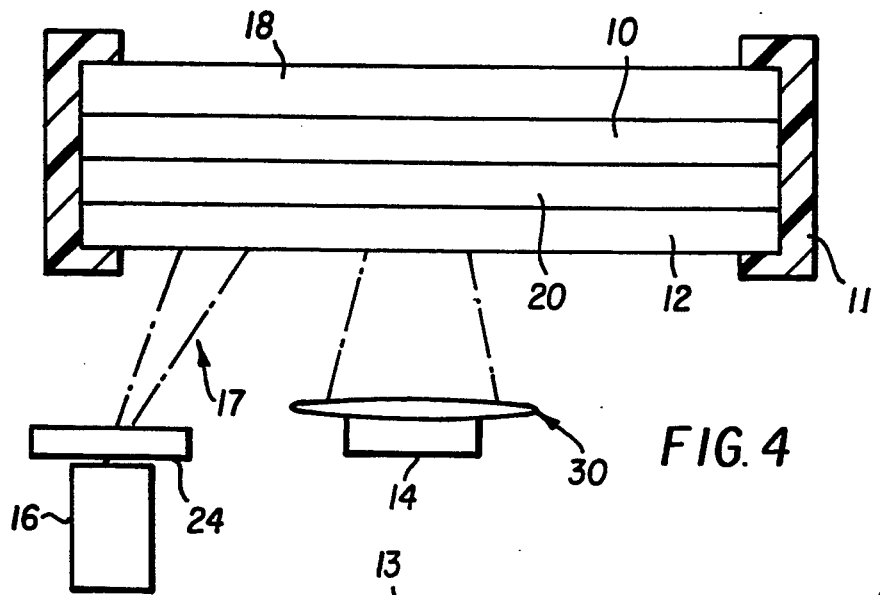
FIG. 4 shows a second embodiment of the test element according to the invention.

FIG. 4 shows a structure similar to FIG. 3 where the excitation radiation source 16 is modulated by a modulator 24 and the upconverted radiation is focused onto a detector 14 by optics 30, after it interacts with the reagent layer 20.

Figure 5:
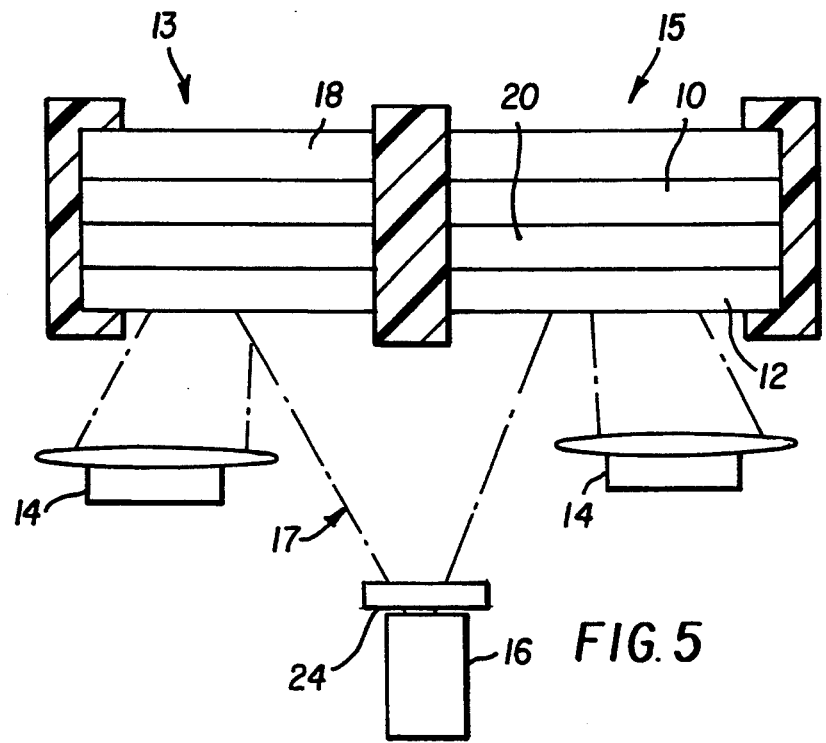
FIG. 5 represents a third embodiment of the test element of the present invention.

FIG. 5 shows an arrangement where two similar layered structures 13, 15 are integrated onto the same slide.

Figure 6:
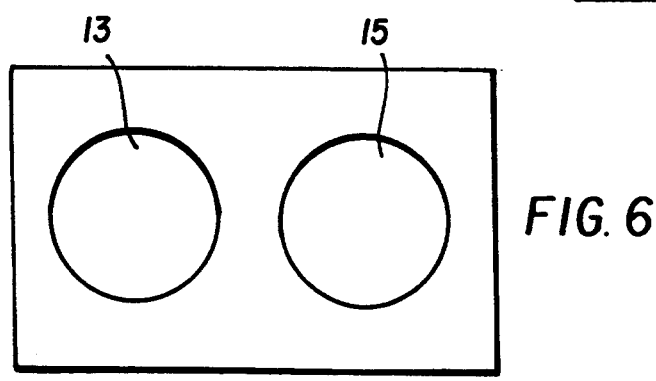
FIG. 6 shows a top view of the structure illustrated in FIG. 5.

FIG. 6 illustrates the top view of the embodiment shown in FIG. 5. One side 15 serves as a reference site (without analyte) and the other 13 as the actual test site (with analyte). Excitation radiation 17 is directed to both of them and the upconverted radiation produced by the upconversion phosphor material 10 on each side of the integral test element are sampled and compared for purposes of quantifying the analyte.

Figure 7:
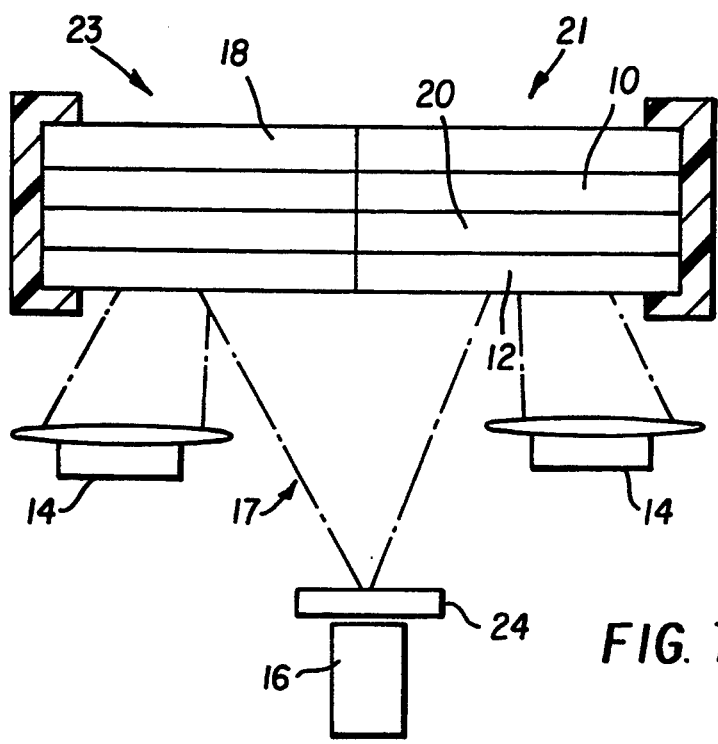
FIG. 7 illustrates a fourth embodiment of the test element of the invention.
Figure 8:
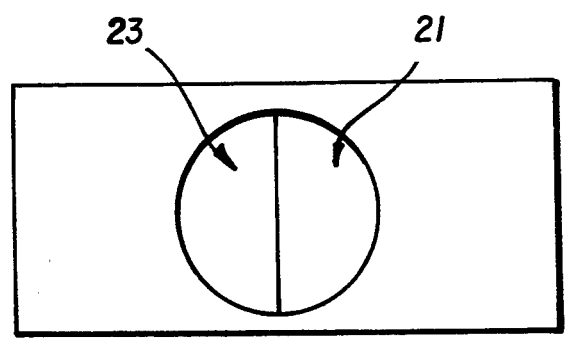
FIG. 8 shows a top view of the structure illustrated in FIG. 7.

FIGS. 7 and 8 show a structure where only half of the test area 23 contains enzyme, indicator or whatever chemical agent that effects the change (for example in color) which is detected. Therefore color change occurs after the interaction with analyte in this half proportional to the concentration of analyte while no color change occurs on the other half 21. By sampling both halves concurrently or sequentially the quantity of analyte can be determined in a self referencing manner.

Figure 9:
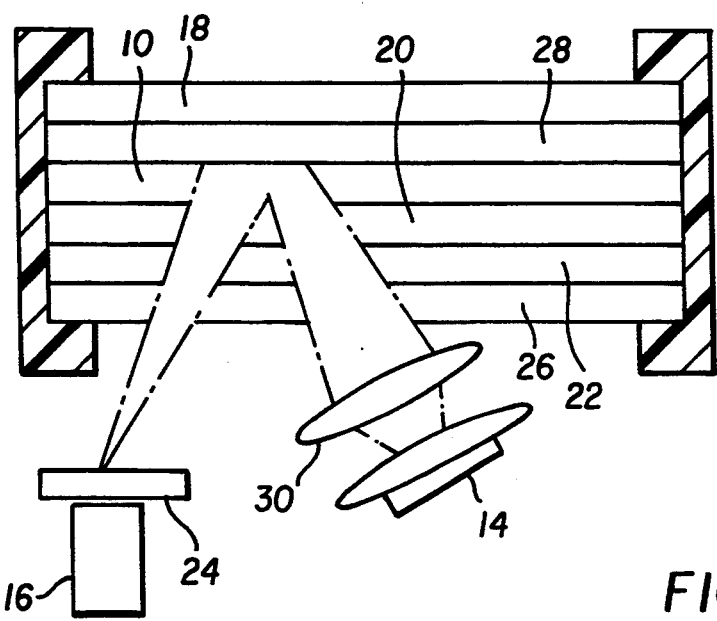
FIG. 9 shows a fifth embodiment of the test element according to the invention.

FIG. 9 shows a structure similar to FIG. 3 where an IR antireflection coating 26 has been applied to ensure that the majority of the excitation radiation passes onto the layered structure and onto the upconversion phosphor material. A reflection coating (UV-visible) 28 is provided on the opposite side of the slide so that it will reflect a majority of the upconverted radiation out toward the detector 14.

The drawings illustrate various embodiments of the invention. It is recognized that a multiplicity of optical coatings may be deposited onto any of the parts in order to improve the upconversion process and in order to enhance the interaction of the upconverted radiation with the analyte. It is also recognized that a multiplicity of optical elements can be used in order to focus, collimate, separate and direct the upconverted radiation as well as the source of irradiation (LED or diode Laser). It is to be further understood that the irradiation source as well as the detector may be configured to interact with the upconversion phosphor material from opposite sides of the slide, by means of optical couplings connected to fiber optics or by any such means in a manner that provides the most convenient result.

The invention has been described in detail with particular reference to certain preferred embodiments thereof, but it will be understood that variations and modifications can be effected within the spirit and scope of the invention.

PARTS LIST 10 upconversion phosphor material
11 slide mount
12 support or substrate
13 test site
14 detector
15 reference site
16 LED or diode laser
17 excitation radiation
18 Spreading layer
20 Reagent layer
21 first half of the test area
22 Cap
23 second half of the test area
24 Modulator
26 IR antireflection coating
28 UV-visible reflection coating
30 Focusing optics
47 lamp
48 upconversion device
50 infrared filter
52 mirror
54 aperture arrangement
56 lens
58 slide
59 photodetector
60 collimated lens assembly
62 relay lens assembly
64 filter wheel

We claim:

1. An integral test element for determination of an analyte in a liquid comprising:
   a) a spreading layer for uniformly spreading within itself at least a portion of a liquid sample applied to the element;
   b) a reagent layer in fluid contact with said spreading layer and permeable to said analyte spreadable within said spreading layer or to a reaction product of said analyte, said reagent layer having a chemically interactive material which, in the presence of said analyte or of said reaction product of the analyte, produces a detectable change in the element; and c) a radiation upconversion phosphor layer or crystal for producing upconverted radiation when excited by visible or infrared excitation radiation from an independent source, wherein said upconverted radiation interacts with said sample or analyte, absorbing a characteristic radiation wavelength ($\lambda$) in a manner proportional to the concentration of the analyte in the liquid.

2. The integral test element according to claim 1 wherein the upconversion phosphor layer or crystal is crystalline or amorphous and contains a rare-earth metal fluoride capable of interacting with red or infrared radiation and converting such to ultraviolet or visible radiation.

3. The integral test element according to claim 2 wherein the rare-earth metal fluoride is a mixed metal fluoride selected from the group consisting of alkaline fluorides, alkaline earth fluorides, and lanthanide fluorides.

4. The integral test element according to claim 1 further including a reflection layer to reflect said upconverted radiation.

5. The integral test element according to claim 1 further including an antireflection layer to maximize the absorption of the excitation radiation by said upconversion phosphor layer or crystal.

6. The integral test element according to claim 1 wherein said element defines two separate adjacent multilayer sites, a test site and a reference site, wherein the test site has spreading and reagent layers and a radiation upconversion phosphor and the reference site differs from the structure of said test site in that it has no reagent layer.

7. The integral test element according to claim 1 including an evaporation prevention cap and wherein said radiation upconversion layer or crystal is supported by the evaporation prevention cap so that when said cap and said supported radiation upconversion layer are positioned on the test element, they define with the spreading layer, the reagent layer and the radiation upconversion layer a one-piece test element.

* * * * *